US007294133B2

(12) United States Patent
Zink et al.

(10) Patent No.: US 7,294,133 B2
(45) Date of Patent: Nov. 13, 2007

(54) METHOD AND APPARATUS FOR PREPARING A GLENOID SURFACE

(75) Inventors: Robert W. Zink, Warsaw, IN (US); Roy C. Wiley, Warsaw, IN (US); Gregory P. Nicholson, Western Springs, IL (US); Michael Pearl, Los Angeles, CA (US)

(73) Assignee: Zimmer Technology, Inc., Chicago, IL (US)

( * ) Notice: Subject to any disclaimer, the term of this patent is extended or adjusted under 35 U.S.C. 154(b) by 149 days.

(21) Appl. No.: 11/143,529

(22) Filed: Jun. 2, 2005

(65) Prior Publication Data

US 2006/0058809 A1 Mar. 16, 2006

Related U.S. Application Data

(60) Provisional application No. 60/577,145, filed on Jun. 3, 2004.

(51) Int. Cl.
*A61B 17/58* (2006.01)
(52) U.S. Cl. ...................................... 606/96
(58) Field of Classification Search ............ 606/80–81, 606/86–87, 96–99, 102, 104; 623/19.11–19.13
See application file for complete search history.

(56) References Cited

U.S. PATENT DOCUMENTS

| | | | |
|---|---|---|---|
| 4,708,139 A | 11/1987 | Dunbar, IV | |
| 4,986,833 A | 1/1991 | Worland | |
| 4,998,937 A | 3/1991 | Grimes | |
| 5,030,219 A | 7/1991 | Matsen, III et al. | |
| 5,344,458 A | 9/1994 | Bonutti | |
| 5,437,677 A * | 8/1995 | Shearer et al. | ................ 606/96 |
| 5,489,310 A | 2/1996 | Mikhail | |
| 5,593,448 A * | 1/1997 | Dong | ...................... 623/19.11 |
| 5,665,090 A | 9/1997 | Rockwood et al. | |
| 5,681,333 A | 10/1997 | Burkhart et al. | |
| 5,769,856 A | 6/1998 | Dong et al. | |
| 5,779,710 A | 7/1998 | Matsen, III | |
| 5,800,551 A | 9/1998 | Williamson et al. | |
| 5,885,297 A | 3/1999 | Matsen, III | |
| 5,961,555 A | 10/1999 | Huebner | |

(Continued)

OTHER PUBLICATIONS

Zimmer Bigliani/Flatow the Complete Shoulder Solution - Total Shoulder Arthroplasty Surgical Technique, Bigliani et al., Copyright 1999, 2000, 2003.

*Primary Examiner*—Eduardo C. Robert
*Assistant Examiner*—Anitza M San Miguel
(74) *Attorney, Agent, or Firm*—Baker & Daniels LLP

(57) ABSTRACT

A method and apparatus for facilitating shoulder arthroplasty by providing a reference to establish version of the glenoid. In one form of the invention, a guide for positioning a guide pin to facilitate implantation of a glenoid prosthesis is provided. To properly position the guide pin, the guide is first oriented with respect to the scapula. A portion of the guide is positioned over the approximate center of the glenoid surface and another portion of the guide is positioned against the anterior surface of the scapula. After the guide is properly positioned, the guide pin is inserted through an aperture in the guide and anchored in the glenoid. Thereafter, the guide pin can serve as an alignment guide for other devices used to modify the glenoid surface. For example, a reamer having a cannulated central shaft can be placed over the guide pin and utilized to resurface the glenoid.

14 Claims, 6 Drawing Sheets

U.S. PATENT DOCUMENTS

| | | |
|---|---|---|
| 6,102,953 A | 8/2000 | Huebner |
| 6,168,627 B1 | 1/2001 | Huebner |
| 6,168,628 B1 | 1/2001 | Huebner |
| 6,193,758 B1 | 2/2001 | Huebner |
| 6,206,886 B1 | 3/2001 | Bennett |
| 6,228,120 B1 | 5/2001 | Leonard et al. |
| 6,231,611 B1 | 5/2001 | Mosseri |
| 6,277,123 B1 * | 8/2001 | Maroney et al. ............ 606/102 |
| 6,364,910 B1 * | 4/2002 | Shultz et al. ............ 623/19.13 |
| 6,375,684 B1 | 4/2002 | Kriek |
| 6,482,237 B2 | 11/2002 | Mosseri |
| 6,589,281 B2 | 7/2003 | Hyde, Jr. |
| 6,620,197 B2 | 9/2003 | Maroney et al. |
| 6,656,225 B2 | 12/2003 | Martin |
| 6,676,706 B1 | 1/2004 | Mears et al. |
| 6,716,249 B2 | 4/2004 | Hyde |
| 6,780,190 B2 | 8/2004 | Maroney |
| 6,783,548 B2 | 8/2004 | Hyde, Jr. |
| 6,953,478 B2 * | 10/2005 | Bouttens et al. ......... 623/19.11 |
| 6,962,593 B2 | 11/2005 | Sanford |
| 6,984,248 B2 | 1/2006 | Hyde |
| 2002/0138148 A1 | 9/2002 | Hyde, Jr. |
| 2003/0050704 A1 | 3/2003 | Keyan |
| 2003/0149486 A1 | 8/2003 | Huebner |
| 2003/0171757 A1 | 9/2003 | Coon et al. |
| 2003/0212403 A1 | 11/2003 | Swanson |
| 2004/0015173 A1 | 1/2004 | Erving |
| 2004/0034431 A1 | 2/2004 | Maroney et al. |
| 2004/0064189 A1 | 4/2004 | Maroney et al. |
| 2004/0153066 A1 | 8/2004 | Coon |
| 2005/0021038 A1 | 1/2005 | Maroney |
| 2005/0043805 A1 | 2/2005 | Chudik |
| 2005/0085919 A1 | 4/2005 | Durand-Allen et al. |

* cited by examiner

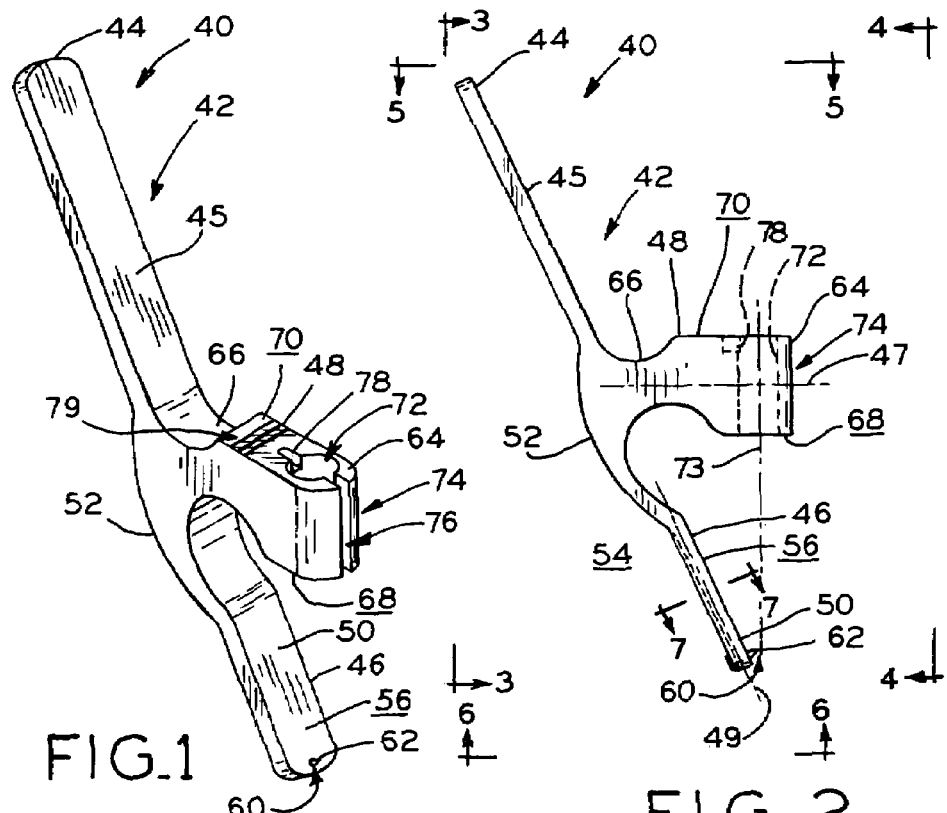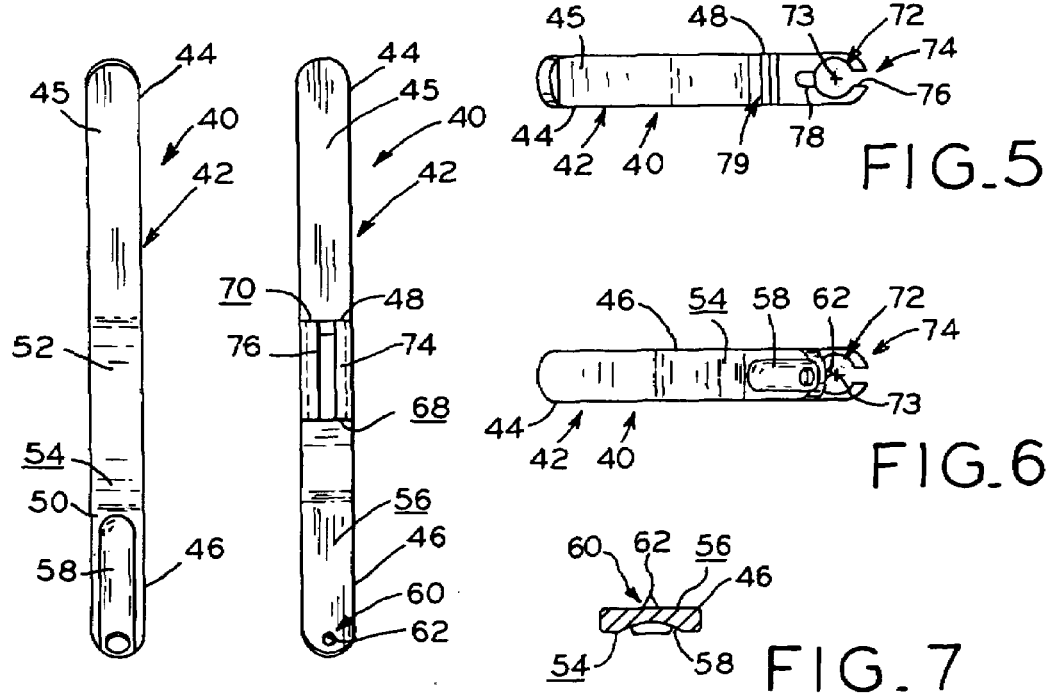

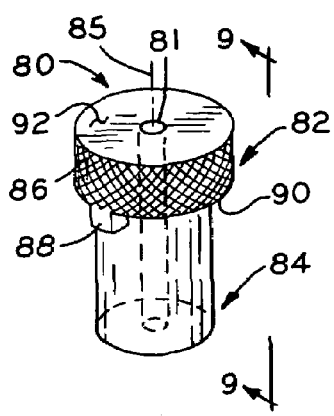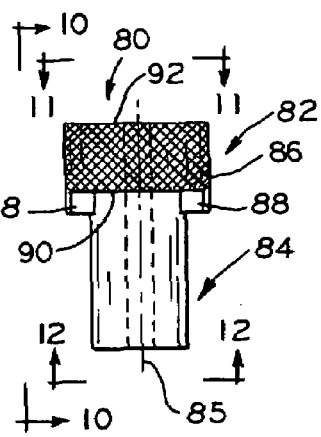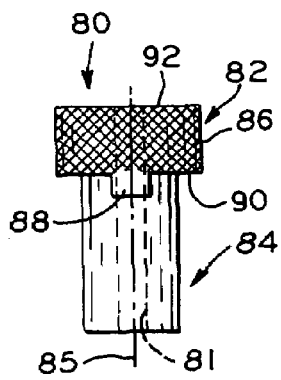
FIG. 8    FIG. 9    FIG. 10
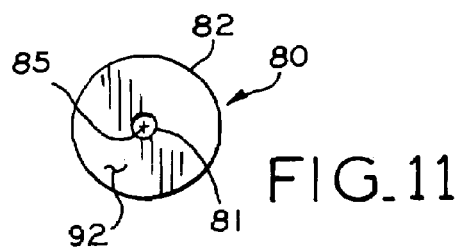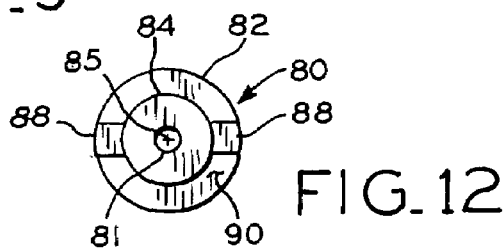
FIG. 11    FIG. 12
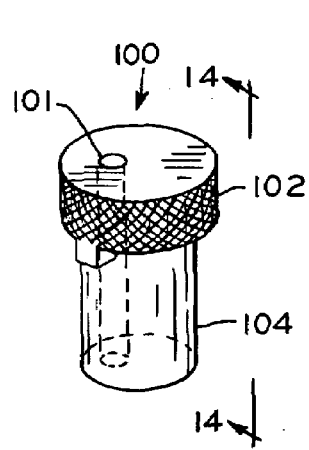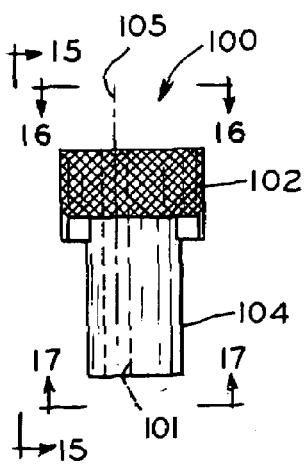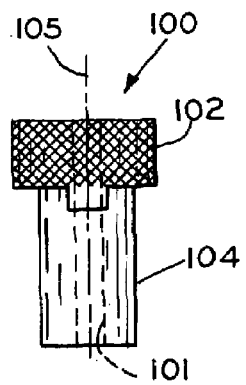
FIG. 13    FIG. 14    FIG. 15
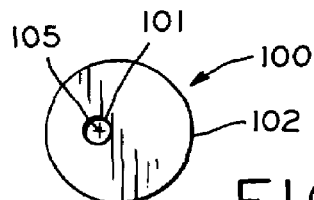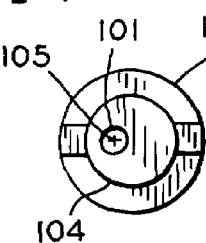
FIG. 16    FIG. 17

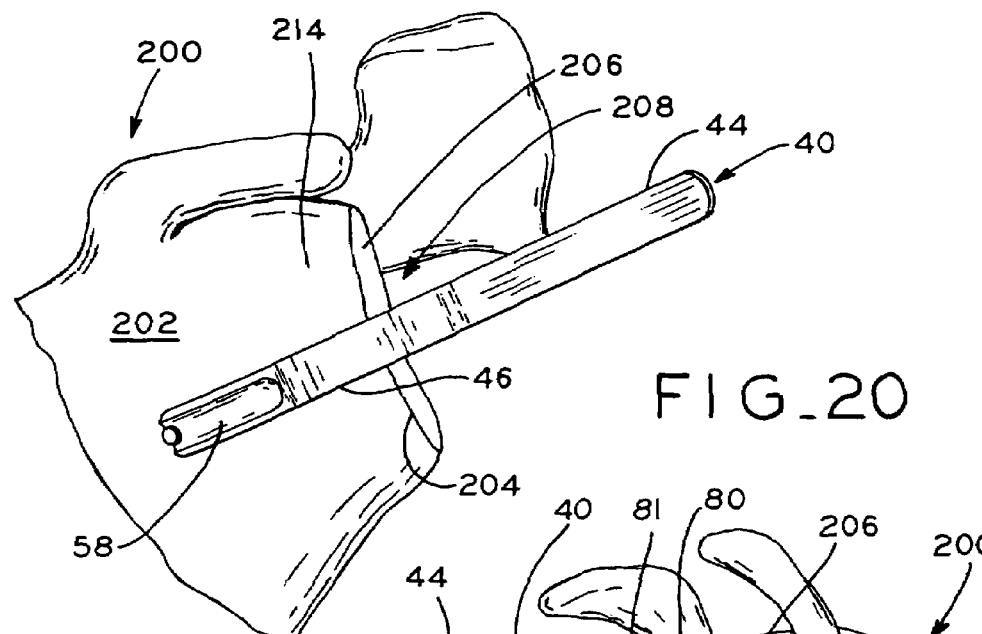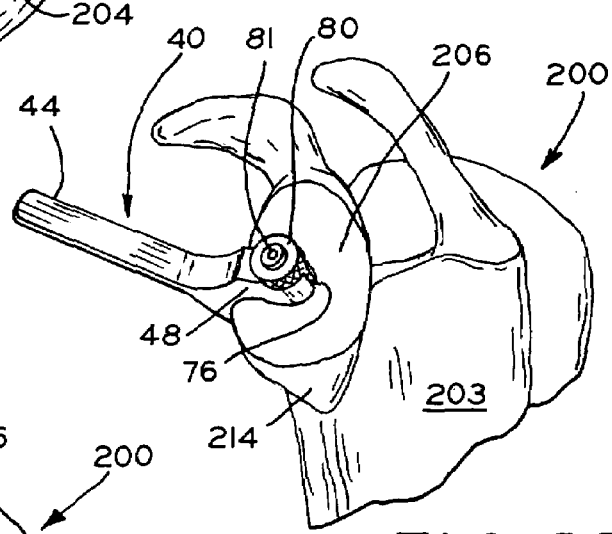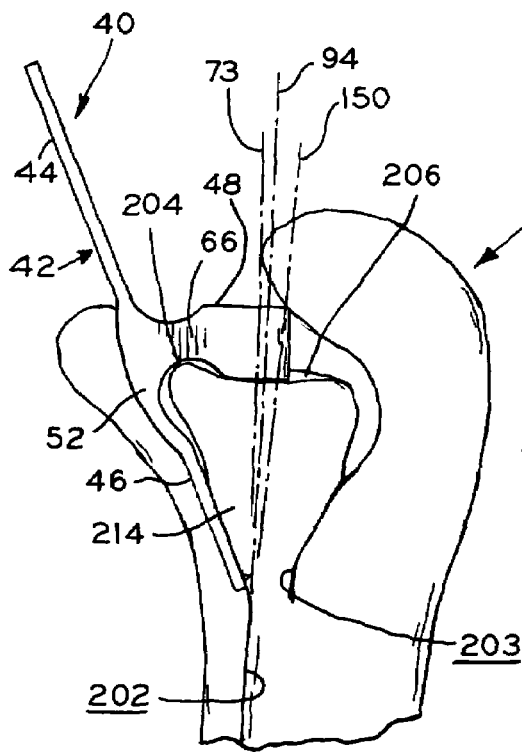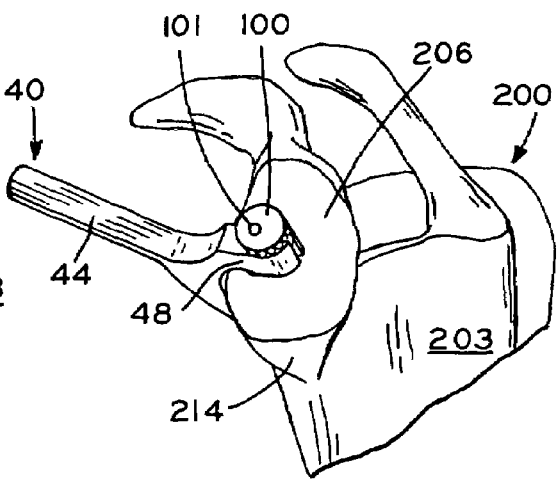
FIG._20
FIG._21
FIG._22
FIG._23

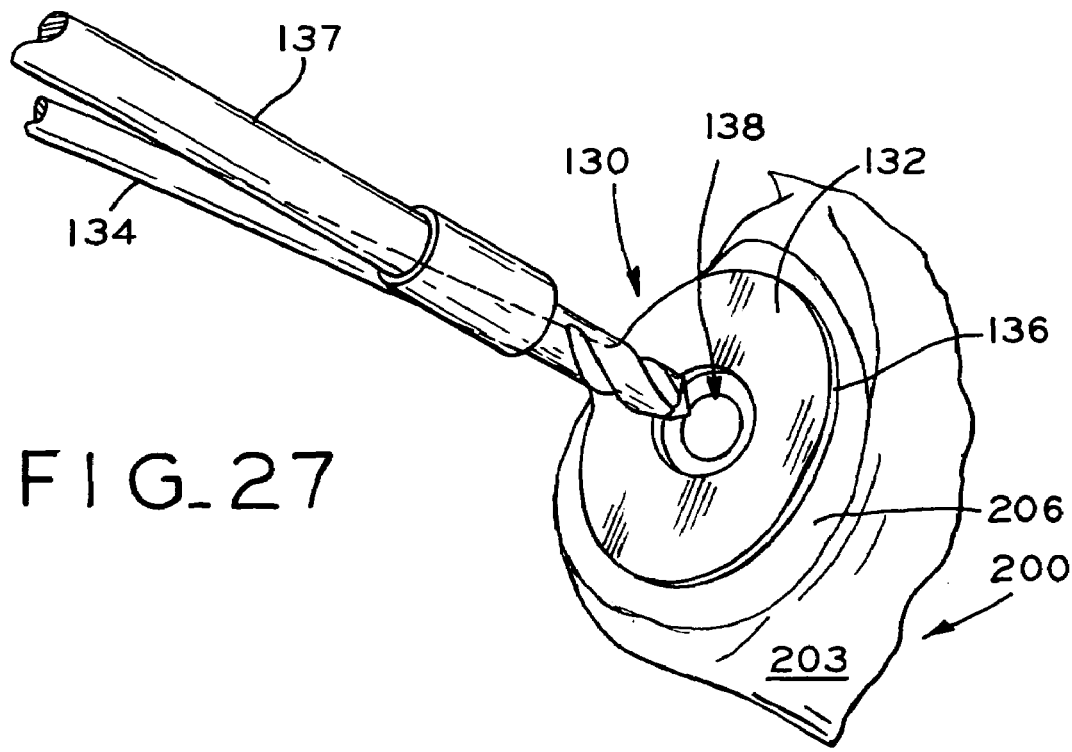
FIG_27
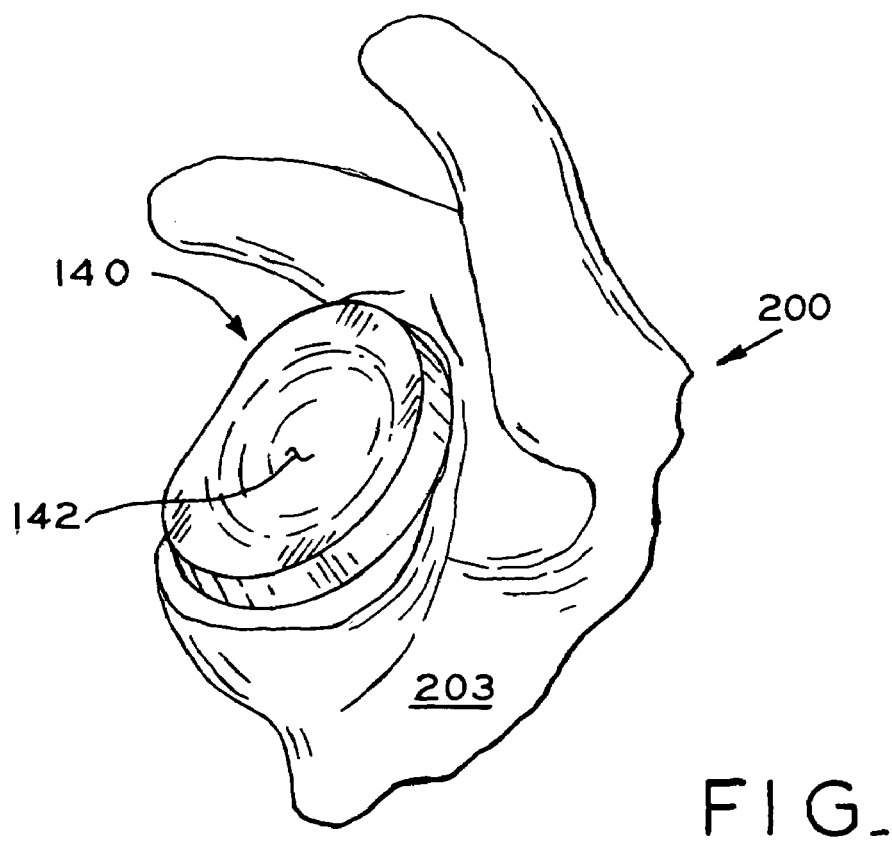
FIG_28

METHOD AND APPARATUS FOR PREPARING A GLENOID SURFACE

CROSS REFERENCE TO RELATED APPLICATION

This nonprovisional patent application claims priority under 35 U.S.C. §119(e) to co-pending U.S. provisional patent application Ser. No. 60/577,145 filed Jun. 3, 2004, the disclosure of which is hereby explicitly incorporated by reference herein.

BACKGROUND

1. Field of the Invention

The present invention generally relates to the field of orthopaedics, and, more particularly, to a method and apparatus for providing a reference to establish version in a glenoid of a scapula.

2. Description of the Related Art

The shoulder or glenohumeral joint allows for articulation between the glenoid or socket of the scapula and the head of the humerus. In a healthy shoulder, articular cartilage covers the articular portions of the humeral head and the glenoid to facilitate movement in the shoulder joint. A natural shoulder may degenerate for a variety of reasons. For example, the articular cartilage may wear. Degenerative changes to the shoulder anatomy may necessitate replacement of all or part of the natural shoulder with prosthetic shoulder components. For example, the natural humeral head may be replaced with a prosthetic humeral component. The glenoid may also be replaced with a prosthetic glenoid component. When glenoid replacement is indicated, the glenoid may be resurfaced and shaped to accept the prosthetic glenoid component. The glenoid component generally includes an articular surface which is engaged by the humeral head. When implanting a prosthetic glenoid component, surgeons seek to position the glenoid prosthesis to achieve proper version, i.e., proper alignment of the glenoid prosthesis with the surrounding anatomical structures.

SUMMARY

The method and apparatus of the present invention facilitates shoulder arthroplasty by providing a reference to establish version of the glenoid. In one form of the invention, a guide for positioning a guide pin to facilitate implantation of a glenoid prosthesis with proper version is provided. To properly position the guide pin, the guide is first oriented with respect to the scapula. In one embodiment, to orient the guide to facilitate placement of the guide pin, a portion of the guide is aligned with the approximate center of the glenoid surface while another portion of the guide references the anterior surface of the scapula. In this position, the guide can assist a surgeon in positioning a reference element indicative of proper glenoid version. In one embodiment, after the guide is positioned, the guide pin is inserted through an aperture in the guide and anchored in the glenoid. In one embodiment, the guide pin is inserted into the glenoid along an axis that is substantially collinear with the scapular neck axis. In one embodiment, the guide pin is drilled into the glenoid surface and the guide is then removed. Thereafter, the guide pin can serve as an alignment guide for, e.g., devices used to modify the glenoid surface. In one embodiment, a reamer having a cannulated central shaft is placed over the guide pin and utilized to resurface the glenoid. The guide pin may further be used to guide instruments useful for preparing the glenoid to have a glenoid prosthesis anchored therein.

The invention, in one form thereof, comprises a method of providing a reference to establish version of a glenoid of a scapula including the steps of: aligning a guide with the glenoid, the guide including an anterior scapula contact surface, the step of aligning a guide with the glenoid comprising the steps of: establishing a glenoid reference point on the glenoid surface; aligning the guide with the glenoid reference point; and positioning the anterior scapula contact surface in contact with an anterior scapula reference point, the anterior scapula reference point and the glenoid reference point defining a guide axis substantially collinear with the neck axis.

The invention, in another form thereof, comprises a guide for establishing the orientation of a guide axis relative to a glenoid surface. In this form of the present invention, the guide comprises a body including a guide portion and a reference portion, the guide portion configured to extend over the glenoid surface, the guide portion including a guide aperture, the guide aperture defining the guide axis, the reference portion configured to extend over an anterior surface of the scapula, the reference portion including a contact point for contacting the anterior surface of the scapula, wherein the contact point is substantially located on the guide axis. In one embodiment of the present invention, the guide body includes a slot transverse to the guide aperture, the slot extending from the guide aperture through an outside surface of the guide body.

The invention, in a further form thereof, comprises a system for locating a position on a glenoid surface of a scapula, the scapula including an anterior surface. The system of this form of the present invention includes a guide comprising a body including a guide portion and a reference portion, the guide portion including an aperture, the guide portion configured to extend over the glenoid surface, the reference portion configured to extend over the anterior surface of the scapula; and a bushing, the bushing positioned in the body aperture, the bushing including an aperture. The system of this form in the present invention further includes a guide pin passable through the bushing aperture, the guide pin including an insertion end for engaging the glenoid surface and a shaft, wherein the bushing is removable from the body when the guide pin is positioned in the bushing aperture by passing the bushing along the shaft.

BRIEF DESCRIPTION OF THE DRAWINGS

The above-mentioned and other features of this invention, and the manner of attaining them, will become more apparent and the invention itself will be better understood by reference to the following description of an exemplary embodiment of the invention taken in conjunction with the accompanying drawings, wherein:

FIG. 1 is a perspective view of a guide in accordance with the present invention;

FIGS. 2–6 are elevational views of the guide of FIG. 1;

FIG. 7 is a cross-sectional view of the guide of FIG. 1 taken along line 7—7 in FIG. 2;

FIG. 8 is a perspective view of a guide bushing in accordance with the present invention;

FIGS. 9–10 are radial elevational views of the guide bushing of FIG. 8;

FIGS. 11–12 are axial elevational views of the guide bushing of FIG. 8;

FIG. 13 is a perspective view of a second guide bushing in accordance with the present invention;

FIGS. 14–15 are radial elevational views of the guide bushing of FIG. 13;

FIGS. 16–17 are axial elevational views of the guide bushing of FIG. 13;

FIG. 20 is a partial anterior view of the scapula and guide depicted in FIG. 19;

FIG. 21 is a partial superior view of the scapula and guide depicted in FIG. 19;

FIG. 22 is a partial perspective view of the scapula and guide depicted in FIG. 19, with the bushing depicted in FIGS. 7–12 placed in an aperture in the guide;

FIG. 23 is a partial perspective view of the scapula and guide depicted in FIG. 19, with the bushing depicted in FIGS. 13–17 placed in an aperture in the guide;

FIG. 27 is a perspective view of a preliminary drill guide and a drill; and

FIG. 28 is a perspective view of a glenoid prosthesis positioned over the glenoid.

Figure 18:
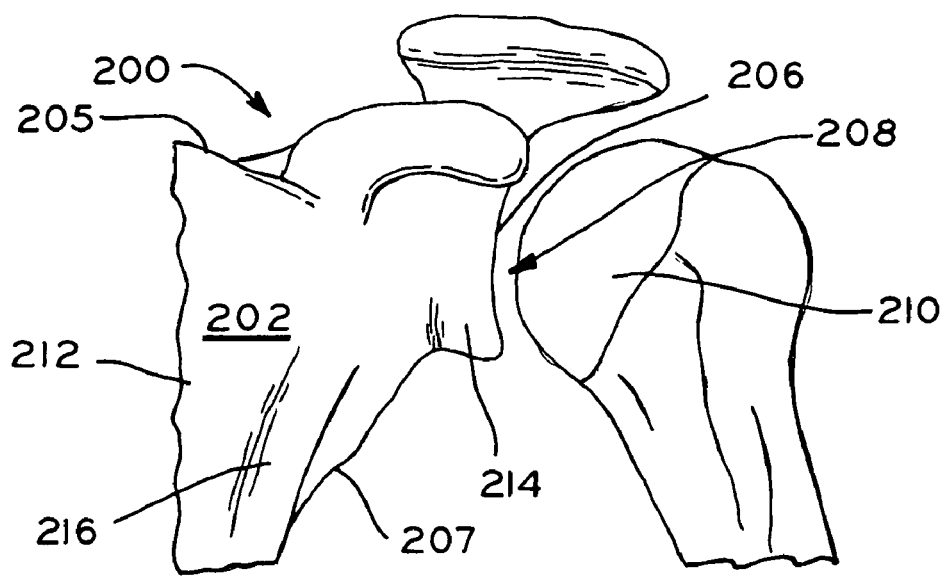
FIG. 18 is a partial anterior view of the anatomy of the left shoulder of a human.
Figure 19:
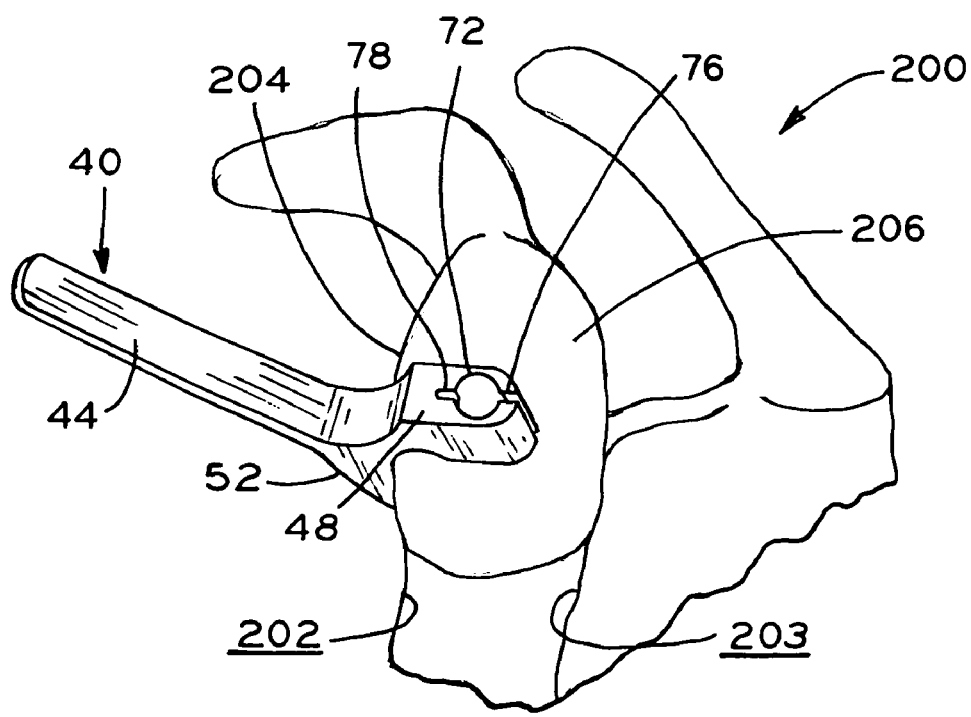
FIG. 19 is a partial lateral view of a left human scapula with the guide of FIG. 1 positioned thereon.

Corresponding reference characters indicate corresponding parts throughout the several views. Although the drawings represent an exemplary embodiment of the present invention, the drawings are not necessarily to scale and certain features may be exaggerated to better illustrate and explain the present invention. The exemplification set out herein illustrates an exemplary embodiment of the invention and such exemplification is not to be construed as limiting the scope of the invention in any manner.

DETAILED DESCRIPTION

The present invention will now be described with reference to the attached figures. The description below may include reference to the following terms: anterior (at or near the front of the body, as opposed to the back of the body); posterior (at or near the back of the body, as opposed to the front of the body); lateral (at or near the left or right side of the body, farther from the midsagittal plane, as opposed to medial); medial (in the middle, at or near the midsagittal plane, as opposed to lateral); proximal (toward the beginning, as opposed to distal); and distal (further from the beginning, as opposed to proximal).

Glenoid replacement may be necessary when, e.g., the bone stock of the glenoid and/or cartilage covering the glenoid becomes worn. A surgical technique for glenoid replacement incorporating an exemplary method and apparatus of the present invention is disclosed in BIGLIANI/FLATOW THE COMPLETE SHOULDER SOLUTION Trabecular Metal Glenoid Surgical Technique With Cannulated Instruments, distributed by Zimmer, Inc., Warsaw, Ind., a copy of which is attached as an appendix hereto, the disclosure of which is hereby explicitly incorporated by reference herein.

Referring to FIGS. 18–26, human scapula 200 includes anterior surface 202 and posterior surface 203. Scapula 200 includes three borders, i.e. edges, including superior border 205 and an axillary border 207. Scapula 200 further includes three angles at the apices of the borders, including lateral angle 208 at the apex of superior border 205 and axillary border 207. Scapula 200 includes glenoid surface 206 at lateral angle 208 for articulating with a proximal head of humerus 210. Scapula 200 further includes subscapular fossa 212 (FIG. 18) on anterior surface 202, neck portion 214 adjacent glenoid surface 206, and ridge 216 intermediate neck portion 214 and subscapular fossa 212.

In one embodiment of the present invention, a glenoid prosthesis is properly implanted after establishing proper version of glenoid surface 206. As discussed in further detail below, a guide may by used to determine the version of the glenoid by referencing at least one point on the glenoid face and at least one point on the anterior surface of the scapula. In one embodiment, the guide is then used to engage a guide pin with the glenoid. As discussed in further detail below, the guide pin can serve as an alignment guide for subsequent steps of preparing the glenoid surface to, e.g., receive a glenoid implant.

Referring to FIGS. 1–7, guide 40 includes body 42. Body 42 includes handle 44, reference arm 46 and guide arm 48. Reference arm 46 includes substantially straight, elongate portion 50 and arcuate portion 52. Portion 50 includes anterior-facing surface 54 and posterior-facing surface 56. Anterior-facing surface 54 may include an ergonomic recess or channel 58 (FIG. 3) configured to accommodate a surgeon's finger, e.g., a surgeon's index finger, to assist the surgeon in positioning guide 40. Reference arm 46 may further include projection 60 extending from posterior-facing surface 56. As illustrated in FIG. 21, and described in detail below, arcuate portion 52 is configured to provide clearance between guide body 42 and anterior edge 204 of glenoid 206. While the presently described exemplary guide includes a body having elongate reference and guide arms, other embodiments are contemplated which have reference and guide portions having other geometries capable of carrying out the goals and aims of the invention. For example, in one embodiment, the body of the guide may comprise an arcuate member having a guide portion at one end of the member and a reference portion at the other end of the member.

In the illustrated embodiment the curve of arcuate portion 52 extends into handle 44, however, this is not an essential feature of the claimed invention. Handle 44 includes substantially straight portion 45 which is substantially aligned with substantially straight portion 50 of reference arm 46. Guide arm 48 extends from the intersection of handle 44 and reference arm 46. Referring to FIG. 2, axis 47 of guide arm 48 and axis 49 of reference arm 46 define an angle of approximately 65 degrees. However, other angles are contemplated. For example, in embodiments having reference arms longer than reference arm 46 of the present embodiment, the angle may increase. In other embodiments having reference arms shorter than reference arm 46, the angle may decrease. Guide arm 48 includes portion 64 at the end of guide arm 48 and portion 66 adjacent arcuate portion 52 of reference arm 46. Similar to arcuate portion 52, proximal portion 66 provides clearance between the guide and the numeral head and surrounding tissues.

Posterior portion 64 includes two opposing substantially flat surfaces, glenoid-facing surface 68 and bushing stop surface 70. In one exemplary embodiment, Posterior portion 64 further includes a rounded distal end 74 and guide body aperture 72 extending between surfaces 68 and 70. Posterior portion 64 further includes slot 76 extending transversely from guide body aperture 72 to rounded end 74. Guide body aperture 72 defines axis 73. As illustrated in FIG. 2, sharp tip 62 is, in one exemplary embodiment, provided on projection 60 in a position substantially along axis 73. As discussed further below, in this embodiment, guide body aperture 72, with a bushing placed therein, will guide a pin as it is drilled into glenoid surface 206 (FIG. 24) substantially along axis 73. Because tip 62 is positioned substantially along axis 73, a surgeon may use tip 62 as a reference point indicating the approximate orientation of the drill axis. As explained in detail further below, slot 76 assists a surgeon in removing the guide from the surgical site after a guide pin has been engaged with the glenoid surface. Posterior portion 64 further includes indexing recess 78 for limiting relative rotational movement between the guide and a bushing when the bushing is positioned in guide body aperture 72, as explained in detail below.

A first embodiment of a bushing is illustrated in FIGS. 8–12. Bushing 80 includes head portion 82 and shaft portion 84. In this embodiment, head portion 82 and shaft portion 84 are both substantially cylindrical, however, in other embodiments, these portions may include any geometry sufficient to carry out the goals and aims of the present invention. In this embodiment, head portion 82 is substantially concentric with shaft portion 84. Head portion 82 may optionally include knurled perimeter 86 for assisting a surgeon in holding and placing bushing 80 into guide body aperture 72. Shaft portion 84 is sized to closely fit within guide body aperture 72. Bushing 80 further includes alignment projections 88 extending radially at the conjunction of head portion 82 and shaft portion 84. When shaft portion 84 is inserted into guide body aperture 72 of guide 40, in order to seat bottom surface 90 of head portion 82 against bushing stop surface 70 of guide arm 48, bushing 80 must be oriented such that alignment projections 88 are aligned with slot 76 and indexing recess 78. If alignment projections 88 are not aligned with slot 76 and indexing recess 78, bottom surface 90 of head portion 82 cannot be seated against bearing stop surface 70, as alignment projections 88 will bear against bushing stop surface 70. Additionally, the proper engagement of alignment projections 88 with slot 76 and recess 78 prevents substantial relative rotation between bushing 80 and guide 40. To prevent head portion, 82 from passing through guide body aperture 72, head portion 82 has a substantially larger diameter than guide body aperture 72. Bushing 80 further includes bushing aperture 81 extending through the center of head portion 82 and shaft portion 84. Accordingly, aperture 81 will substantially remain in the center of bushing 80 regardless of the degree of rotation of bushing 80 within guide body aperture 72 and, as a result, alignment projections 88, in this embodiment, are not needed to prevent relative rotation between bushing 80 and guide 40. However, in other embodiments, as discussed in detail below, the bushing aperture may be offset from the center of the bushing and projections 88 may be needed to prevent relative rotation between guide 40 and the bushing. In this embodiment, it is important that bottom surface 90 of head 82 be seated against bearing stop surface 70, as top surface 92 of head 82 is used as a datum to assist the surgeon in determining the proper depth to seat the alignment pin. In one embodiment, the alignment pin may include a colored band or indentation that, when aligned with top surface 92 of bushing 80, indicates to the surgeon that the proper depth of the alignment pin has been achieved. Other embodiments are envisioned in which top surface 92 provides a physical stop preventing further insertion of the guide pin. A method of using guide 40 and bushing 80 in shoulder arthroplasty will now be described.

In one exemplary method of shoulder arthroplasty, the glenoid vault, i.e., the concave region of the glenoid is initially evaluated. This initial evaluation can be performed using an axillary radiograph to assess for anterior or posterior wear of the glenoid. If a radiograph is not possible, a CT or MRI can be obtained to provide this information. Therafter, an incision is made and the soft tissues surrounding the shoulder are retracted both anteriorly and posteriorly to expose the shoulder joint. A Fukuda Retractor, or a bent glenoid retractor can be placed posteriorly to subluxate the humerus posteriorly and inferiorly. A pointed Darrach-type Retractor can be placed anteriorly. To access the glenoid, the humeral head is then severed. Thereafter, the capsule, i.e., the membrane or sac enclosing the shoulder joint, is stripped from the articular margin of the glenoid. Tight shoulders may necessitate the release of the capsule along the inferior margin of the glenoid, taking care to avoid injury to the axillary nerve. Release of the posterior capsule, which is often already stretched out from chronic posterior humeral subluxation, is not routinely performed to avoid posterior prosthetic instability. In rare cases of extremely tight shoulders, some posterior release may be helpful.

After exposing and distracting the shoulder as described above, the orientation of the glenoid face with respect to the scapular neck and the center of the glenoid surface can then be determined. To determine the orientation of the glenoid face with respect to the scapular neck, the surgeon may place their finger along the anterior surface of the neck. As will be discussed in detail further below, determining the relative orientation of the scapular neck and the glenoid face facilitates the proper orientation of the glenoid prosthesis. Determination of the center of the glenoid surface may be difficult as osteophytes growing from the perimeter of the glenoid surface may disguise the center. The surgeon can choose to trim any marginal osteophytes so the glenoid surface can be clearly defined. Sometimes, osteophytes are more pronounced on one side of the glenoid surface than on the other. In such cases, the center of the articular surface, including osteophytes, is not the center of the glenoid surface. It is not necessary to remove all the osteophytes to establish the true center of the glenoid, however, if any osteophytes are removed, they should be removed carefully. In particular, removal of posterior osteophytes should be done with caution as the capsular attachments may be more proximal resulting in instability.

Generally, as illustrated in FIGS. 19–23, after the glenoid has been exposed, guide arm 48 of guide 40 is placed over glenoid surface 206 and reference arm 46 is positioned along anterior surface 202 of scapula 200. More particularly, to position guide 40 for the subsequent steps discussed below, the surgeon first visually identifies the center of glenoid surface 206. A sizing guide may be used to facilitate identification of the center of glenoid surface 206. Guide body aperture 72 of guide arm 48 is then substantially aligned with the center of glenoid surface 206 and reference arm 46 is guided between the anterior surface of the scapula and the soft tissue anterior of the scapula. In one form of this method, guide body aperture 72 is substantially aligned with the center of glenoid surface 206 and reference arm 46 is guided between scapula 200 and the soft tissue at substantially the same time. In another form of this method, the surgeon may place glenoid-facing surface 68 of guide arm 48 against glenoid surface 206 and rotate guide 40 such that reference arm 46 clears glenoid anterior edge 204. In doing so, guide 40 may translate slightly so that guide body aperture 72 will need to be realigned with the center of glenoid surface 206. In another form of this method, reference arm 46 may be positioned over the anterior scapula and guide arm 48 is thereafter rotated in the position with aperture 72 substantially aligned with the center of glenoid surface 206. Alternatively, the surgeon may hold guide arm 48 suspended above glenoid surface 206 while positioning reference arm 46 against anterior surface 202 of scapula 200 and thereafter move guide arm 48 into abutment with glenoid reference 206, with guide body aperture 72 substantially aligned with the center of glenoid 206, while moving reference arm 46 along anterior surface 202 of scapula 200. Guide arm 48 is positioned with respect to glenoid surface 206 such that guide arm 48 substantially bisects glenoid anterior edge 204. Stated in another way, taking the glenoid surface as a clock face, with the superior most point of the glenoid being 12 o'clock, guide arm 48 is substantially aligned with 9 o'clock when used in a left shoulder and is substantially aligned with 3 o'clock when used in a right shoulder.

As described above, it may be possible to guide reference arm 46 along anterior surface 202 of scapula 200 before placing guide arm 48 over glenoid surface 206. However, referring to FIG. 21, neck 214 projects significantly from the scapula and, as a result, the anatomy of neck 214 reduces the possible approaches of reference arm 46 around anterior edge 204. Accordingly, a less pronounced neck 214 may allow a surgeon to position guide 40 in this manner.

To position reference arm 46, a surgeon may place a finger, e.g., the index finger, along anterior-facing surface 54 of reference arm 46 to insert guide reference arm 46 between the soft tissue anterior of the scapula and the anterior surface of the scapula. Channel 58 is configured to assist the surgeon in holding guide 40. In one exemplary embodiment, the distal end of the surgeon's finger is positioned proximate projection 60 such that the surgeon can press sharp tip 62 into the scapula once the proper position and orientation of guide body 40 has been determined. Tip 62 is placed on scapular ridge 214 (FIG. 18), i.e, on the medial aspect of the glenoid vault.

To position body aperture 72, or more specifically, axis 73 of aperture 72, over the center of the glenoid surface, a surgeon may elect to visually determine the center of the glenoid surface and/or use a preliminary drill guide. An exemplary preliminary drill guide, i.e., guide 130, is illustrated in FIG. 27 and includes head portion 132 and handle portion 134. Head portion 132 includes perimeter 136 that substantially parallels the outer edge, or perimeter, of a typical glenoid surface. To properly postion head portion 132, a surgeon can visually align and substantially center perimeter 136 within the outer edge of the glenoid. Head portion 132 further includes guide aperture 138 which, once perimeter 136 has been aligned with the glenoid edge, should be substantially centered over the center of the glenoid surface. A surgeon can then drill into glenoid surface 206 with a drill, such as small starter drill 137 (FIG. 27), to mark the substantial center of glenoid surface 206.

In this form of the invention, once guide 40 has been positioned in the above-described manner, axis 73 of guide body aperture 72 extends through the substantial center of glenoid surface 206. As discussed above, tip 62 of reference arm 46, is also substantially positioned on axis 73. Thus, when tip 62 is positoned against anterior surface 202 of scapula 200, axis 73 extends between a reference point on the glenoid, i.e., the center of glenoid surface 206, and a reference point on anterior surface 202 of scapula 200, i.e., the point contacted by tip 62. Owing to this relationship, and the selection of the reference points on the scapula, in this form of the invention, as illustrated in FIG. 21, axis 73 is substantially collinear with an axis defined by the scapular neck, i.e., axis 94. Accordingly, guide aperture 72 can substantially align a guide pin or a drill bit, etc., along neck axis 94. When referring to axis 73 as "substantially collinear" with axis 94 of the scapular neck, it is contemplated that axis 73 may form an angle of up to 10° with axis 94. It is further contemplated that axis 73 may be offset a small distance from axis 94. The guide pin and/or drilled hole can be used to establish proper version of a glenoid prosthesis. For example, in one embodiment, a glenoid prosthesis having a peg can be inserted into the hole. Further, substantially aligning axis 73 with scapular neck axis 94 substantially orients the guide pin between the anterior and posterior cortical walls of scapular neck 214, thereby reducing the possibility of the guide pin penetrating these cortical walls.

Determining the version of the glenoid face according to the method and apparatus of the present invention facilitates proper alignment of a glenoid prosthesis when it is implanted into the glenoid. A surgeon viewing the glenoid surface, without referencing the scapular neck, may have difficulty in determining proper glenoid version. For example, as illustrated in FIG. 21, a surgeon, viewing glenoid surface 206 from a lateral incision, may perceive that an axis perpendicular to the glenoid face, i.e., axis 150, is the axis of the scapular neck. The guide of the present invention assists the surgeon in establishing proper version of glenoid face 206 by referencing scapular neck 214.

Once guide 40 has been positioned with respect to glenoid surface 206 as described above, bushing 80 can be positioned within guide body aperture 72, as illustrated in FIG. 22. Shaft portion 84 of bushing 80 closely fits within aperture 72 of guide 40 such that center axis 85 of bushing aperture 81 will remain substantially collinear with axis 73 of guide body aperture 72. Accordingly, as a result of positioning guide 40 in the above-discussed manner, axis 85 of bushing aperture 81 will also be substantially collinear with scapula neck axis 94.

However, on occasion, as a result of anatomical differences between patients, axis 73 of guide aperture 72, and therefore axis 85 of bushing aperture 81, cannot be aligned over the center of the glenoid in the above-discussed manner. To account for these anatomical differences, alternative bushings may be provided having apertures, and corresponding aperture axes, off-set from axis 73 of guide body aperture 72. One such bushing, bushing 100, is depicted in FIGS. 13–17. Bushing 100 includes bushing aperture 101 having axis 105 that is off-set from the centers of head portion 102 and shaft portion 104 thereof. As a result, as illustrated in FIG. 23, when bushing 100 is positioned in guide body aperture 72, axis 105 is off-set from, but substantially parallel to, axis 73 of guide body aperture 72.

A plurality of bushings can be provided so that a surgeon can select a bushing that has an aperture that substantially aligns over the center of the glenoid surface. According to one method of the present invention, a surgeon can place guide 40 over the glenoid as discussed above. Based on the observations of the surgeon, the surgeon may determine that axis 73 of guide body aperture 72 does not align with the center of glenoid surface 206. In this event, the surgeon can select a bushing having an off-set hole, such as bushing 100 described above, and insert it into guide aperture 72. The surgeon can then evaluate whether axis 105 of aperture 101 is aligned with the center of the glenoid. If it is not, the surgeon can select a different bushing and repeat the above steps. Once the surgeon is satisfied with the alignment of the bushing aperture with the center of the glenoid, the surgeon can proceed to the following steps.

Figure 24:
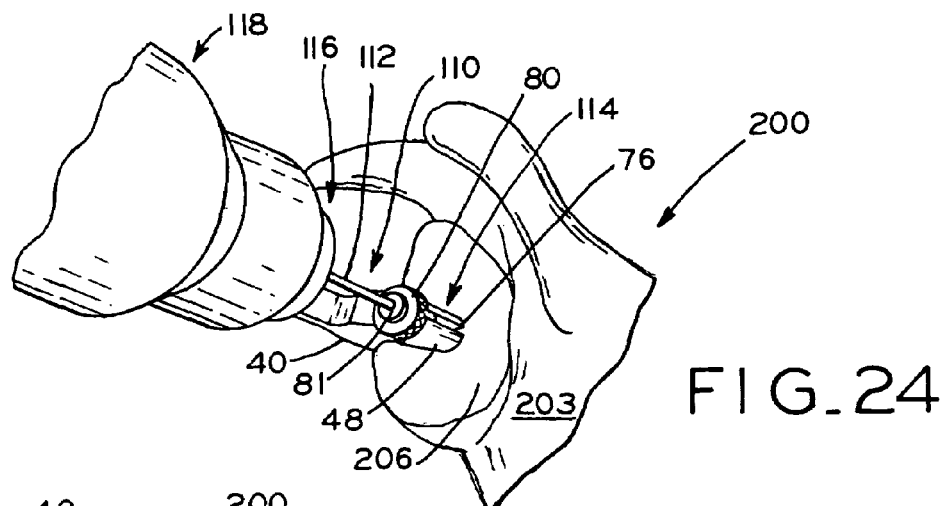
FIG. 24 is a partial perspective view of a guide pin being drilled into a glenoid surface, the guide pin being guided by the guide and bushing depicted in FIG. 22.
Figure 25:
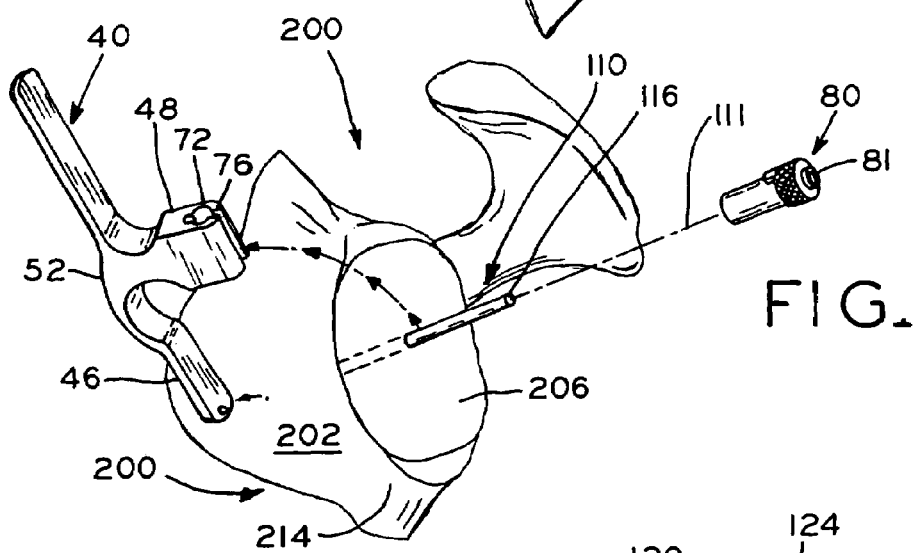
FIG. 25 is a partial, exploded, perspective view illustrating removal of the bushing and the guide from the guide pin of FIG. 24.

Referring to FIG. 24, once guide 40 and an appropriate bushing have been positioned relative to the glenoid and scapula as discussed above, guide pin 110 is inserted into the bushing aperture. In one exemplary embodiment, guide pin 110 includes shaft 112 and cutting end 114 configured to drill into the glenoid surface. Guide pin 110 further includes a drill attachment end 116 configured to be received in the chuck of a drill, such as drill 118. In this embodiment, after guide pin 110 is drilled into the scapula through the center of the glenoid, the drill chuck is released from guide pin 110 and the drill is removed from the surgical site. Thereafter, referring to FIG. 25, the bushing is removed along axis 111 of guide pin 110. Guide 40 can also be removed along axis 111, or, in combination, guide 40 can be rotated away from guide pin 110 such that guide pin 110 passes through lateral slot 76 of guide 40.

Figure 26:
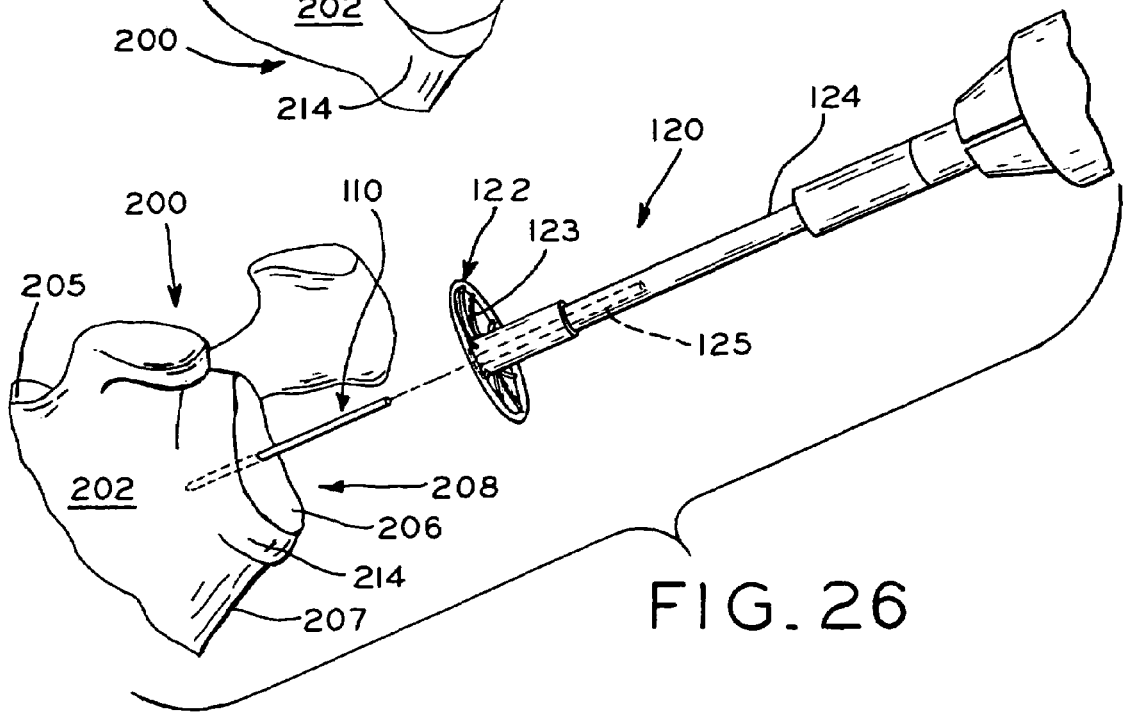
FIG. 26 is a partial, exploded, perspective view of a cannulated reamer positioned for insertion over a guide pin anchored in the scapula.

Once guide 40 and the bushing have been removed from guide pin 110, guide pin 110 can serve as an alignment guide for other instruments or procedures performed to prepare the glenoid surface to receive a glenoid prosthesis. In particular, as illustrated in FIG. 26, guide pin 110 provides an alignment guide for cannulated reamer 120. Cannulated reamer 120 includes cutting head 122 and shaft 124 for transmitting rotational motion to cutting head 122. Cutting head 122 includes blades 123 positioned circumferentially around cutting head 122. Cannulated reamer 120 further includes aperture 125 extending through head 122 into shaft 124 and is configured to receive guide pin 110. Cannulated reamer 120 can be used to remove any remaining cartilage and substantially smooth and/or level the bone stock of the glenoid. Additionally, guide pin 110 can serve as an alignment guide for a cannulated drill bit to drill a hole surrounding guide pin 110, into which a stud of a glenoid prosthesis can be anchored.

After guide pin 110 is no longer needed, it can be removed using drill 118 leaving behind a hole in the glenoid surface. Thereafter, this hole can be used to center other instruments and can assist the surgeon in other steps of the surgical technique. For example, a larger hole can be drilled into or chiseled into the glenoid surface for receiving a stud extending from a glenoid prosthesis using the smaller hole as a guide. Thereafter, a glenoid prosthesis is inserted into the glenoid. As illustrated in FIG. 28, glenoid prosthesis 140 includes surface 142 that substantially repicates a healthy glenoid surface and assists in restoring the normal function of a shoulder joint.

In one form of the invention, a plurality of glenoid prostheses having different sizes can be provided to the surgeon. To assist a surgeon in selecting a glenoid prosthesis, guide 40 can include indicia or markings 79 (FIGS. 1 and 5) which correspond to the sizes of available glenoid prostheses. In practice, a surgeon can observe which marking on guide body 40 is closest to the anterior edge of the glenoid surface, or another anotomical landmark in other embodiments, and, based on this observation, select a prosthesis that corresponds with the marking. For example, in one embodiment, three markings are provided which correspond to 40 mm, 46 mm and 52 mm glenoid prostheses. Furthermore, these markings may be color-coded, or possess other distinguishing characteristics, such that the surgeon can readily distinguish the markings. In one embodiment, a black marking is provided which correponds to the 40 mm prosthesis, a white marking is provided which corresponds to the 46 mm prosthesis, and a blue marking is provided which corresponds to the 52 mm prosthesis. Markings 79 can also assist the surgeon in evaluating whether guide 40 has been properly positioned over the glenoid. More specifically, if markings 79 do not substantially coincide with anterior edge 204 of the glenoid, the surgeon may re-evalauate the positioning of guide 40 or examine for abnormalties of scapula 200.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:

1. A method of providing a reference to establish version in a glenoid of a scapula, the glenoid including a glenoid surface, the scapula including an anterior surface, said method comprising the steps of:
    aligning a guide with a glenoid of a scapula, the guide including a glenoid contact surface and an anterior scapula contact surface, said step of aligning a guide with a glenoid of a scapula comprising the steps of:
    establishing a glenoid reference point on the glenoid surface;
    aligning the guide with said glenoid reference point;
    placing the glenoid contact surface of the guide in contact with the glenoid; and
    rotating the guide substantially about said glenoid reference point to move the anterior contact surface of the guide into a position where the anterior scapula contact surface is supported by the scapula, while maintaining alignment of the guide with said glenoid reference point.

2. The method of claim 1, wherein the scapula further includes a scapular neck, the scapular neck defining a neck axis, and wherein said step of rotating the guide about said glenoid reference point to move the anterior scapula contact surface of the guide into a position where the anterior scapula contact surface is supported by the scapula comprises the step of positioning the anterior scapula contact surface in contact with an anterior scapula reference point, the anterior scapula reference point and the glenoid reference point defining a guide axis substantially collinear with the neck axis.

3. The method of claim 2, wherein the anterior scapula contact surface of the guide includes a projection, said method further comprising the step of pressing said projection into the scapula, wherein the engagement of the projection and the scapula substantially prevents relative movement therebetween.

4. The method of claim 1, wherein said guide includes a guide aperture defining an axis, and wherein said step of aligning said guide with said glenoid reference point comprises the step of aligning said guide aperture axis with said glenoid reference point, said method further comprising the steps of:
    placing a bushing in said guide aperture, said bushing including an aperture having an axis,
    aligning a guide pin with said bushing aperture axis,
    inserting said guide pin into said bushing aperture;
    engaging said guide pin with the glenoid surface;
    removing said bushing from said guide pin by sliding said bushing along said guide pin; and
    removing said guide from said guide pin.

5. The method of claim 4, wherein said guide includes a slot transverse to said guide aperture, and wherein said step of removing said guide from said guide pin comprises the step of displacing said guide transversely with respect to said guide pin such that said guide pin passes through said slot.

6. The method of claim 4, further comprising the step of selecting said bushing from a plurality of bushings, said plurality of bushings including a first bushing having a bushing aperture axis that is substantially collinear with said guide aperture axis when said first bushing is placed in said guide aperture and a second bushing having a bushing aperture axis that is substantially parallel with said guide aperture axis when said second bushing is placed in said guide aperture.

7. A method of engaging a guide pin with a glenoid of a scapula, the glenoid including a glenoid surface, said method comprising the steps of:
positioning a guide over the glenoid surface, said guide including an aperture;
positioning a bushing in said guide aperture, said bushing including an aperture;
inserting a guide pin through said bushing aperture;
engaging said guide pin with said glenoid surface;
removing said bushing from said guide by sliding said bushing along said guide pin; and
removing said guide from said guide pin.

8. The method of claim 7, wherein said guide aperture includes a slot transverse to said guide aperture, and wherein said step of removing said guide from said guide pin comprises the step of displacing said guide transversely with respect to said guide pin such that said guide pin passes through said slot.

9. The method of claim 7, further comprising the step of selecting said bushing from a plurality of bushings, said plurality of bushings including a first bushing having a bushing aperture that is substantially concentric with said guide aperture when said first bushing is positioned in said guide aperture and a second bushing having a bushing aperture is eccentric with said guide aperture when said second bushing is positioned in said guide aperture.

10. A method of providing a reference to establish version of a glenoid of a scapula, the glenoid including a glenoid surface, the scapula including an anterior surface, the scapula further including a scapular neck, the scapular neck defining a neck axis, said method comprising the steps of:
aligning a guide with the glenoid of the scapula, the guide including an anterior scapula contact surface, said step of aligning a guide with the glenoid of the scapula comprising the steps of:
establishing a glenoid reference point on the glenoid surface;
aligning the guide with said glenoid reference point; and
positioning the anterior scapula contact surface in contact with an anterior scapula reference point, the anterior scapula reference point and the glenoid reference point defining a guide axis substantially collinear with the neck axis.

11. The method of claim 10, wherein the anterior scapula contact surface of the guide includes a projection, said method further comprising the step of pressing said projection into the scapula, wherein the engagement of the projection and the scapula substantially prevents relative movement therebetween.

12. The method of claim 10, wherein said guide includes a guide aperture defining an axis, and wherein said step of aligning said guide with said glenoid reference point comprises the step of aligning said guide aperture axis with said glenoid reference point, said method further comprising the steps of:
placing a bushing in said guide aperture, said bushing including an aperture having an axis,
aligning a guide pin with said bushing aperture axis,
inserting said guide pin into said bushing aperture;
engaging said guide pin with the glenoid surface;
removing said bushing from said guide pin by sliding said bushing along said guide pin; and
removing said guide from said guide pin.

13. The method of claim 12, wherein said guide includes a slot transverse to said guide aperture, and wherein said step of removing said guide from said guide pin comprises the step of displacing said guide transversely with respect to said guide pin such that said guide pin passes through said slot.

14. The method of claim 12, further comprising the step of selecting said bushing from a plurality of bushings, said plurality of bushings including a first bushing having a bushing aperture axis that is substantially collinear with said guide aperture axis when said first bushing is placed in said guide aperture and a second bushing having a bushing aperture axis that is substantially parallel with said guide aperture axis when said second bushing is placed in said guide aperture.

* * * * *